(12) United States Patent
Murphy et al.

(10) Patent No.: US 6,725,722 B1
(45) Date of Patent: Apr. 27, 2004

(54) METHOD OF INSPECTING TURBINE WHEEL AND BUCKET FINGER DOVETAILS FOR CRACKS

(75) Inventors: Thomas Francis Murphy, Scotia, NY (US); Gerald John Czerw, Scotia, NY (US); Edward Lee Bentzel, Latham, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/361,643

(22) Filed: Feb. 11, 2003

(51) Int. Cl.[7] .............................................. G01N 29/04
(52) U.S. Cl. ............................. 73/628; 73/633; 73/641
(58) Field of Search ........................ 73/602, 597, 598, 73/625, 626, 627, 628, 633, 634, 641, 637

(56) References Cited

U.S. PATENT DOCUMENTS

| | | | | |
|---|---|---|---|---|
| 3,952,581 A | * | 4/1976 | Gottelt | 73/640 |
| 3,960,006 A | * | 6/1976 | Smith | 73/622 |
| 4,229,796 A | * | 10/1980 | Garrett | 702/39 |
| 4,577,507 A | * | 3/1986 | Jestrich et al. | 73/640 |
| 4,757,716 A | * | 7/1988 | Nottingham et al. | 73/623 |
| 5,623,107 A | * | 4/1997 | Patterson et al. | 73/865.8 |
| 6,019,001 A | * | 2/2000 | Schreiner et al. | 73/640 |
| 6,065,344 A | * | 5/2000 | Nolan et al. | 73/629 |

* cited by examiner

Primary Examiner—Hezron Williams
Assistant Examiner—Rose M. Miller
(74) Attorney, Agent, or Firm—Nixon & Vanderhye

(57) ABSTRACT

An ultrasonic probe is used to inspect wheel and bucket dovetails of turbines for cracks in the material surrounding pinholes and pins securing the buckets and wheel to one another. Only a minimum number of pins, for example, one of three radially aligned pins securing the bucket and wheel dovetails to one another at every other circumferential position of the pins about the wheel may be removed. A phased array ultrasonic probe is inserted into the excavated pinhole and provides a circumferential scan of the finger dovetails to detect cracks in adjacent pinholes. As an alternative, a probe having one or more piezoelectric elements providing one or more radial beams may be mechanically rotated in the pinhole. Statistical sampling may be used as an indicator of crack formation. Thus, in situ inspection is performed without removal of buckets from the wheel and with only a minimum number of pins being removed.

19 Claims, 5 Drawing Sheets

METHOD OF INSPECTING TURBINE WHEEL AND BUCKET FINGER DOVETAILS FOR CRACKS

BACKGROUND OF THE INVENTION

The present invention relates to methods of inspecting the finger dovetails of a turbine wheel and buckets for cracks in the material surrounding pinholes in which pins are received for securing the buckets and wheel to one another and particularly relates to use of a phased array ultrasonic probe for finger dovetail inspection in situ for cracks in the fingers.

In turbines, for example, steam turbines, the rims of the turbine wheels are often provided with axially spaced, annular extending fingers defining dovetails which receive generally complementary-shaped discrete finger dovetails on buckets secured to the wheel. The bucket and wheel dovetails interdigitate with one another and at least two, and typically three, pinholes are aligned axially through bucket and wheel fingers along the margin of the wheel with the pinholes lying along a radius at each bucket location. Pins are axially inserted through the aligned pinholes to maintain the buckets secured to the wheel. It will be appreciated that the pins bear the radial loading of the buckets on the wheel. Over time and extended use, the radial loading may cause stress-related cracks to develop at or in the general region of one or more of the wheel fingers, particularly at the pinholes in the turbine wheel fingers. The stress-related cracks tend to have a generally tangential orientation and typically propagate circumferentially from the pinholes. The cracks sometimes link up with adjacent pinholes. It will be appreciated that crack formation in either one or both of the wheel and bucket finger dovetails provides a potential for failure of the wheel or bucket dovetail, loss of the bucket at speed and damage to the turbine and/or the power station.

This potential for turbine failure has been recognized in the industry. Consequently, periodic inspections of the wheel and bucket finger dovetails are indicated. Periodic inspections can, of course, be performed by disassembly of the buckets from the turbine wheel. However, to disassemble each bucket or even sample buckets from the turbine wheel after usage of the turbine is labor-intensive, time-consuming and, hence, costly. Additionally, the pins securing the buckets to the turbine wheel are oftentimes extremely difficult to remove to release the bucket from the wheel. Typically, the pins are hammered out or a gun with an explosive charge is used to dislodge those particularly hard-to-remove pins. Also, drilling and EDM processes have been used for pin removal. Upon removal of the pins and buckets from the wheel, the finger dovetails may be inspected, e.g., by using magnetic particle testing techniques. After testing, the buckets and pins must be reinstalled in the wheel. Some of the pins, however, may have been damaged upon their removal and must be replaced. Also, magnetic particle inspection requires surface preparation prior to inspection. Further, significant logistic support in the form of cranes, laydown areas and the like is required in order to complete removal, inspection and reinstallation of the pins to secure the buckets to the wheel. Accordingly, there has developed a need for non-destructive in situ inspection of turbine wheel and bucket finger dovetails.

BRIEF DESCRIPTION OF THE INVENTION

Accordingly, and in a preferred embodiment of the present invention, there is provided a method of inspecting in situ material adjacent the pinholes in the finger dovetails of the wheel and buckets for crack formation with removal of only a minimum number of pins and without removing the buckets from the wheel. Thus, pins are removed from the pinholes at preferably regularly spaced intervals about the wheel, e.g., every other bucket, and then only one and preferably the intermediate pin of the three pins securing the bucket to the wheel. Upon removal of the selected pins, an ultrasonic probe, with either one or more discrete elements, or alternately a phased array ultrasonic probe is then inserted into the pinholes to detect crack formation in both circumferentially and radially adjacent pinholes. In the case of an ultrasonic probe with one or more elements, the probe is mechanically rotated in and about the axes of the aligned pinholes, thereby providing a full circumferential scan of the material about the aligned pinholes. The ultrasonic information is then analyzed for detection of cracks.

In the case of the phased array ultrasonic probe, the probe is sized for insertion into the pinholes whereby the ultrasonic beam can be electronically scanned circumferentially without mechanical movement of the probe, i.e., without rotation of the probe about the axis of the pinhole. The ultrasonic beam can also be focused at different distances. The position of the probe can be encoded and combined with the ultrasonic information, enabling accurate imaging of the inspection data for analysis. The combination of mechanically moving the ultrasonic probe in the axial direction and rotating the ultrasonic beam circumferentially by pulsing individual phased array elements, e.g., piezoelectric elements, about the circumference of the probe with appropriate delays, permits a complete scan of the material about the pinhole. By synchronizing the axial scan with the ultrasonic pulsing, a continuous helical scan path can be produced. Alternatively, a circumferential scan can be conducted at one axial distance and the probe can then be incrementally and repeatedly axially advanced to create a plurality of scan/indexing steps to inspect the material adjacent the axial length of the pinhole. It will be appreciated that the ultrasonic beam thus detects crack formations opening into holes adjacent to the pinhole receiving the probe. Crack formation in the pinhole receiving the probe can be ascertained by another testing technique, such as eddy current tests, after withdrawal of the probe. As a consequence of the foregoing, the inspection process can be performed in situ with a minimum number of pins removed from the pinholes and without removal of buckets from the turbine wheel, while still obtaining a high sensitivity to crack detection in the finger dovetails of the wheel and buckets.

As a further technique, the inspection method hereof may involve a sampling of the finger dovetails at intervals about the wheel insufficient to detect all cracks. That is, the ultrasonic sampling probe may be used only in widely-spaced pinholes and therefore not lie in position to detect all cracks. In this manner, a statistical probability of crack formation can be determined, e.g., non-existent, very low, high probability or the like. Once the probe detects any cracks extant in the dovetail material, the cracks can be further investigated, e.g., by removing the bucket and performing other tests to determine the extent of the crack. Also, the inspection interval about the wheel can be reduced to ensure detection of all cracks, rather than just a sampling.

In a preferred embodiment according to the present invention, there is provided a method of inspecting finger dovetails of at least one of a turbine wheel and bucket, the wheel bucket having aligned holes through the finger dovetails for pinning the wheel and bucket to one another, comprising the steps of inserting an ultrasonic probe in a hole of the aligned holes in one of the wheel and the bucket and rotating the probe within and about axes of the aligned holes to electronically scan material about the hole to identify any cracks extant in the material about the hole.

In a further preferred embodiment according to the present invention, there is provided a method of inspecting finger dovetails of at least one of a turbine wheel and bucket, the wheel bucket having aligned holes through the finger dovetails for pinning the wheel and bucket to one another, comprising the steps of inserting a phased array ultrasonic probe in a hole of the aligned holes in one of the wheel and the bucket and actuating the probe to electronically scan material of a finger dovetail of the one wheel and bucket circumferentially about the hole to identify any cracks extant in the material about the hole.

In a further preferred embodiment according to the present invention, there is provided a method of inspecting in situ turbine wheel and bucket dovetails for cracks in materials about pinholes containing pins securing the buckets and wheel to one another, comprising the steps of (a) removing a pin from a pinhole securing one of the buckets to the wheel, (b) inserting a phased array ultrasonic probe into the pinhole and (c) actuating the probe to electronically scan material circumferentially about the pinhole to identify cracks extant in the material about pinholes adjacent to the pinhole receiving the phased array ultrasonic probe.

DETAILED DESCRIPTION OF THE INVENTION

Figure 1:
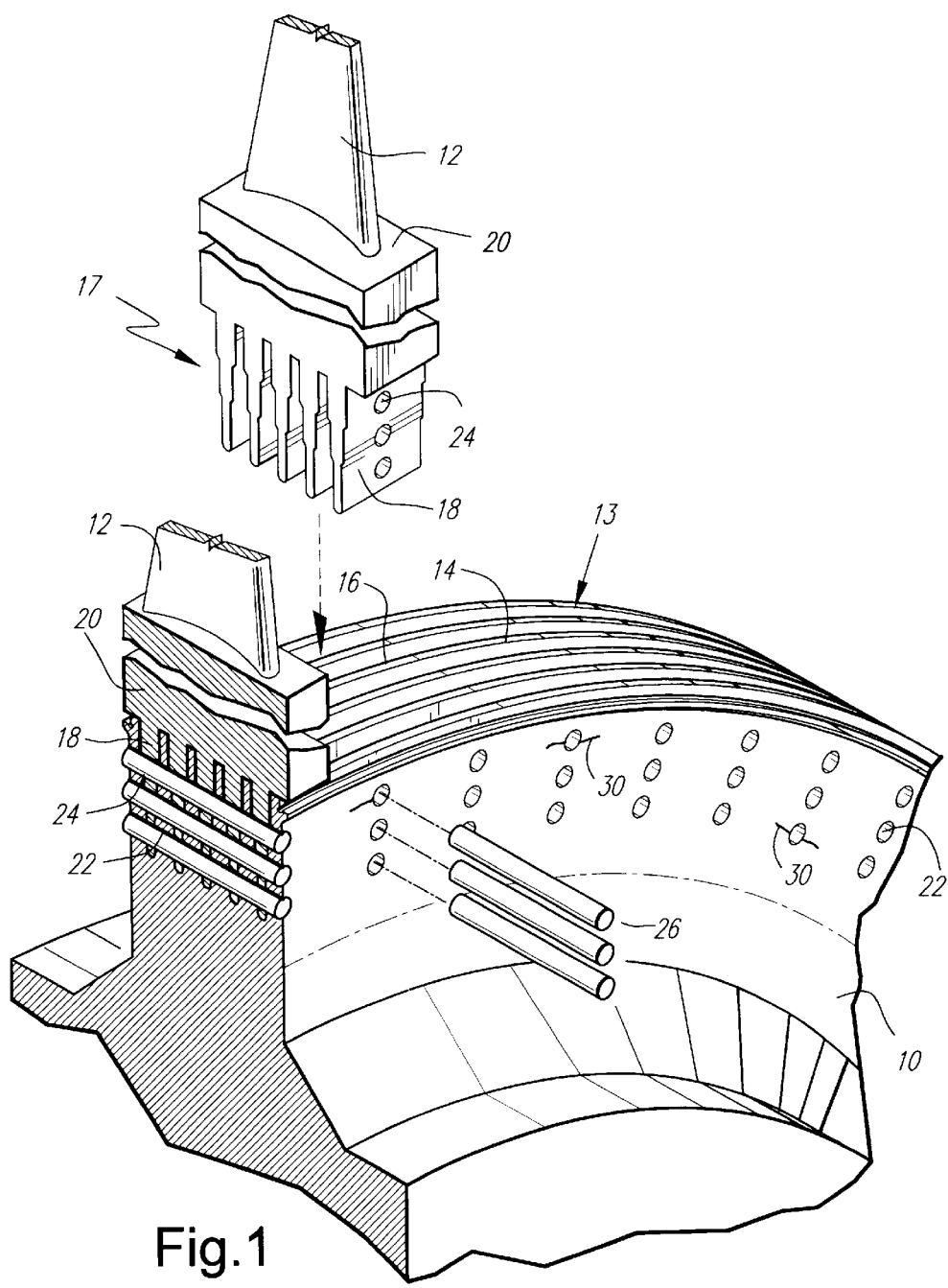
FIG. 1 is a fragmentary perspective view illustrating a portion of the periphery of a turbine wheel and a bucket secured to the wheel.

Referring now to FIG. 1, there is illustrated a rotor wheel 10 for mounting a plurality of buckets 12 about a periphery of wheel 10, only one bucket 12 being illustrated. The rotor wheel 10 includes a circumferentially extending dovetail, generally designated 13, comprised of a plurality of circumferentially extending, radially outwardly projecting fingers 14 defining grooves 16 therebetween. The fingers extend about the entire margin of the wheel 10. The grooves 16 receive a complementary-shaped dovetail, generally designated 17, comprised of a plurality of fingers 18 forming part of the bucket dovetail 20. It will be appreciated that the fingers 14 defining the wheel dovetail 13 interdigitate with the fingers 18 defining the bucket dovetail 17. As illustrated, the projecting fingers of each of the wheel and bucket at each circumferential location of the bucket about the wheel have a plurality of axially extending and registering holes or pinholes 22 and 24, respectively, three radially aligned holes being illustrated for each bucket at each circumferential location of the bucket about the wheel. It will be appreciated that the aligned and registering pinholes 22 and 24 lie along radii of the wheel and are equidistantly circumferentially spaced from one another about the circumference of the wheel. Pins 26 are used to secure the buckets 12 to the wheels 10 and are received through the registering openings 22 and 24. In the illustrated embodiment, three pinholes and, hence, three pins, are provided to secure each bucket to the wheel. It will be appreciated that the bucket dovetails are stacked against one another to form a circumferential array of buckets about the wheel and, in use, the buckets 12 lie in the hot fluid path of the turbine, e.g., the steam path of a steam turbine.

It will be appreciated with reference to FIG. 1 that the centrifugal forces acting on the buckets during turbine operation are resisted by the radially aligned pins 26 and the fingers 14 of the wheel 10. Over time and use, cracks 30 may develop in the fingers 14 and 18 of the wheel and buckets, particularly in the material about the pinhole through the wheel fingers 14. The cracks typically extend in a generally circumferential direction and propagate circumferentially or tangentially, oftentimes propagating from one pinhole to mate up with an adjacent hole. As indicated previously, these cracks can be detected upon disassembly of the buckets from the wheel 10 by removal of the pins 26 and the buckets and utilizing certain test procedures. However, the removal of all of the pins and buckets is a time-consuming, laborious and, hence, costly operation which is avoided in accordance with the present invention.

Figure 2:
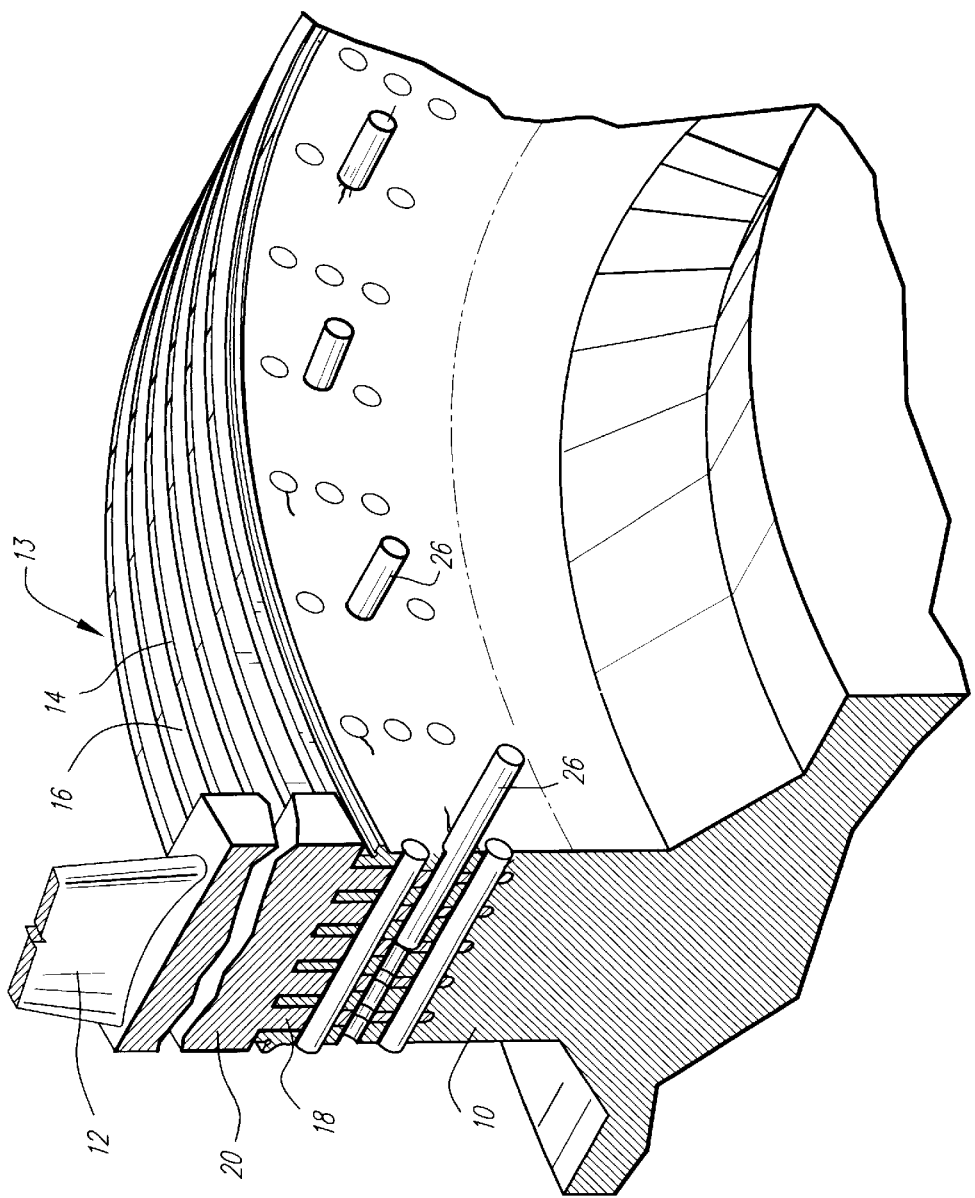
FIG. 2 is a view similar to FIG. 1 illustrating the removal of selected pins in accordance with a preferred method of ultrasonically inspecting the wheel/bucket dovetail according to the present invention.
Figure 3:
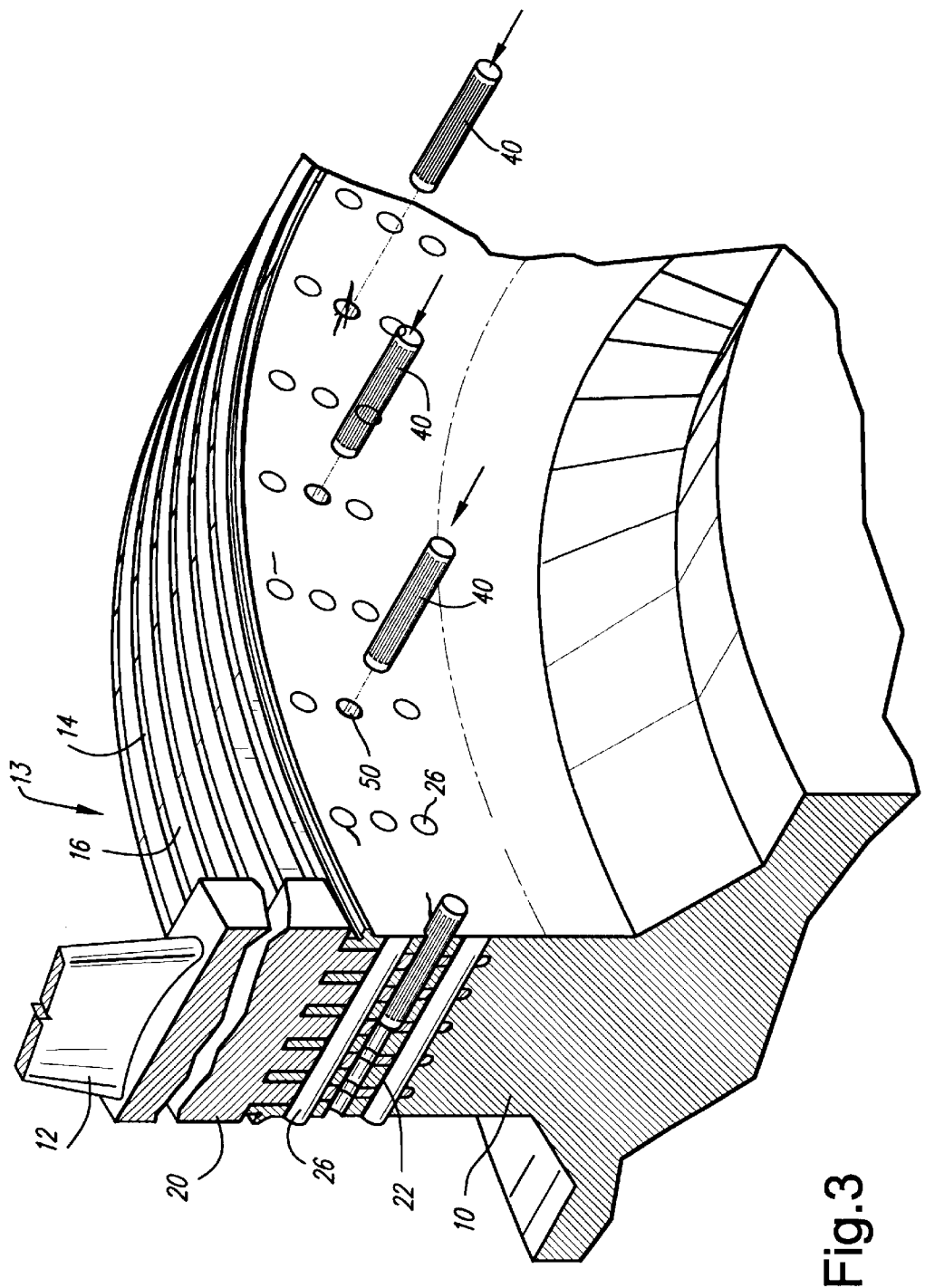
FIG. 3 is a view similar to FIGS. 1 and 2 illustrating the insertion of an ultrasonic probe into the pinholes in which the pins have been removed.

In accordance with a preferred embodiment of the present invention, there is provided a method for inspecting the finger dovetails 13 and 17 in situ, i.e., without removal of the buckets from the margin of the wheel, and by removal of only a very limited number of pins about the wheel. For example, and referring to FIG. 2, initial steps of the preferred method hereof may include the removal of the intermediate pin of the three radially aligned pins holding every other bucket about the margin of wheel 10. The circumferential spacing between the pins removed to enable the present inspection method may include a greater circumferential spacing between the circumferentially spaced pins. For example, the intermediate pin of every third or fourth group of pins about the peripheral margin may be removed. Thus, an intermediate pin of the three radially aligned pins 26 is removed at selected circumferential locations about the margin of the wheel. The pins may be removed by hammering the pins from the aligned pinholes. Alternately, the pins may be drilled out, the gun with an explosive charge may be used to drive one or more of the pins from the pinholes or an EDM process may be used to remove one or more of the pins.

Figure 5:
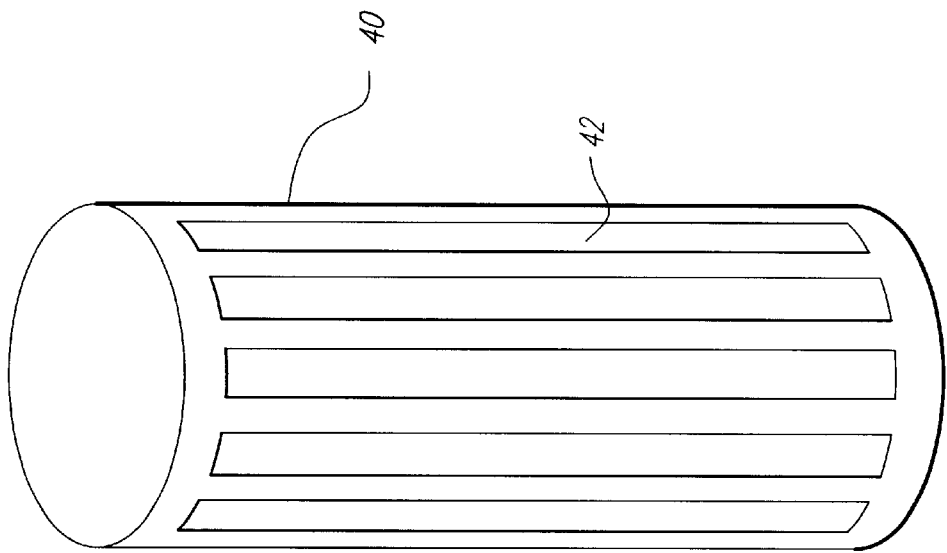
FIG. 5 is a schematic representation of a phased array ultrasonic probe.

Once the pins are removed, a discrete ultrasonic probe having one or more piezoelectric elements or a phased array ultrasonic probe 40 (FIG. 5) may be inserted into the aligned pinholes at each pin-removed hole location to inspect the wheel and bucket finger dovetails for cracks in the material of the dovetails about pinholes adjacent the pinholes receiving the probe. It will be appreciated that, while the probe 40 is described herein as a phased array ultrasonic probe, a probe may also include one or more piezoelectric elements about its surface and which probe requires mechanical rotation in the aligned pinholes to provide the full circumferential scan about the pinhole axes to ascertain the ultrasonic information for analysis and crack detection. In either case, probe 40 is preferably, although not necessarily, cylindrical in configuration to closely align with the circumferential extent of the aligned pinholes. In a preferred embodiment using the phased array ultrasonic probe 40 there is provided a plurality of generally rectangular piezoelectric elements 42 (FIG. 5) spaced one from the other about the periphery of the probe 40. Also as illustrated in FIG. 5, the long dimension of each piezoelectric element 42 lies in the axial direction of the probe. The piezoelectric elements 42 may be curved or flat along their outer surfaces. Dimensionally, the probe has a diameter enabling the probe for insertion into the aligned pinholes with minimum space between the cylindrical surface of the probe and the surfaces of the aligned pinholes to improve resolution. It will be appreciated that the individual piezoelectric elements 42 of the ultrasonic probe may be pulsed with appropriate time delays between the elements 42 to enable creation of an ultrasonic beam which can be focused and steered to interrogate the material surrounding the holes. That is, the ultrasonic beam can be steered 360° around the hole without mechanical rotational movement of the probe about its cylindrical axis. Thus, circumferential scanning of the finger dovetails may be achieved without displacing the probe other than in an axial direction. The combination of displacing the phased array probe in the axial direction by mechanical means, not shown, and rotating the ultrasonic beam electronically in a circle by pulsing the individual elements 42 with appropriate time delays permits a complete scan of the material about the holes. By synchronizing the axial scan with the ultrasonic pulsing, a continuous helical scan pattern can be produced as the probe is continuously axially displaced within the pinholes. Alternatively, a circumferential scan can be conducted at one axial distance and the probe can then be incrementally advanced in the axial direction to create a scan/index coverage path. Either alternative enables complete coverage of the material to be inspected with only one degree of mechanical freedom, i.e., axial motion of the probe.

Figure 6:
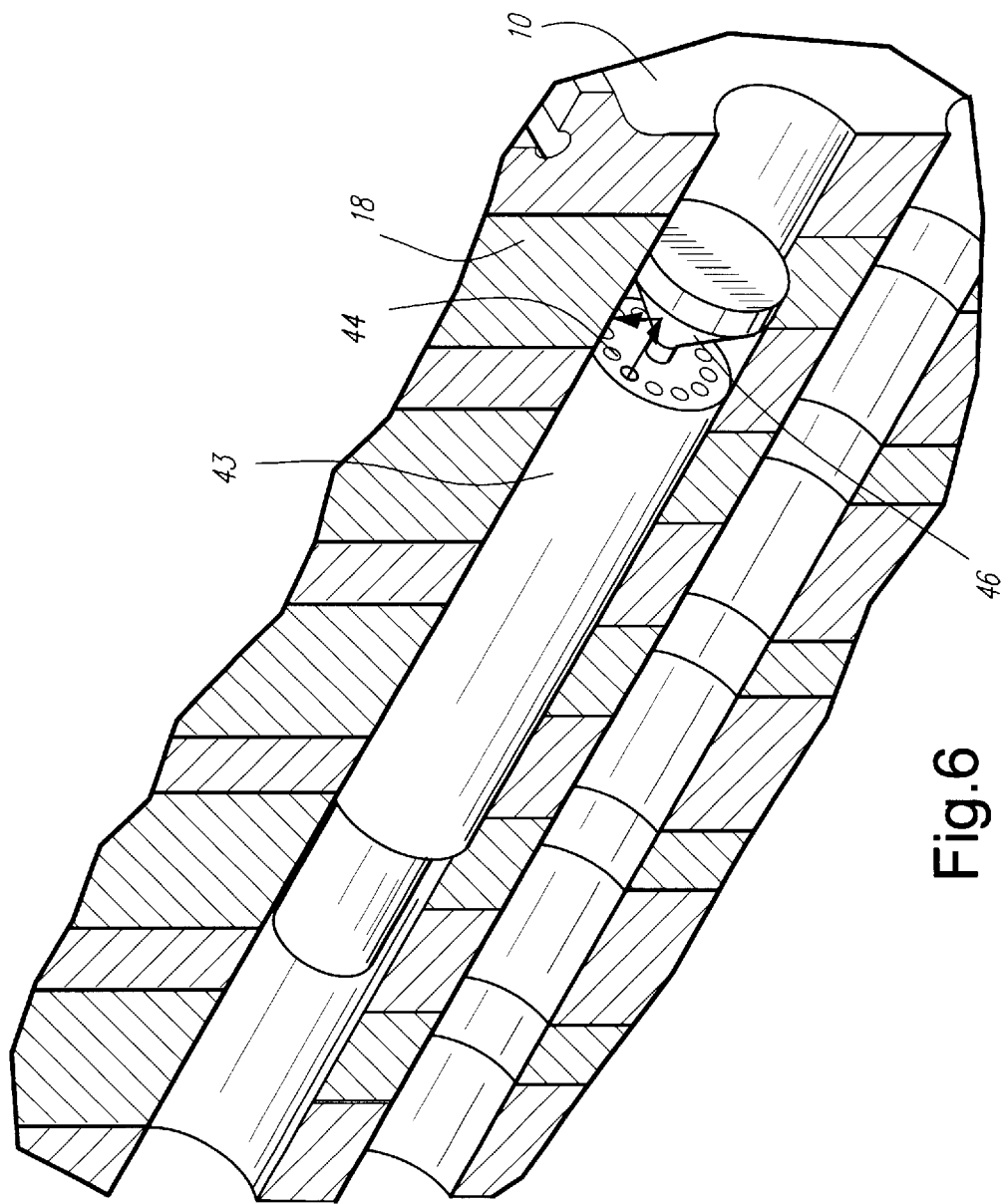
FIG. 6 is a perspective view in cross-section schematically illustrating a different form of a phased array probe in the aligned pinholes.

It will be appreciated that the probe may take other and different forms than the two forms discussed above. For example, and as illustrated in FIG. 6, a further probe 43 may have piezoelectric elements 44 directing ultrasonic energy in an axial direction. The elements 44 are axially aligned with a mirror 46 at one end of the probe, the mirror being conical and disposed at an angle to the axis of the probe 43. The axially extending ultrasonic beam is then reflected off the mirror and thereby directed in a generally radial direction into the finger dovetail material. By pulsing the elements 44 sequentially, the pulsed electronic beam is rotated about the probe axis. It will also be appreciated that the ultrasonic beam can be focused at different distances from the probe. The position of the probe can be encoded and, when combined with the ultrasonic information indicative of a reflection of the beam from a crack back to the probe, enables accurate imaging of the inspection data for analysis.

Figure 4:
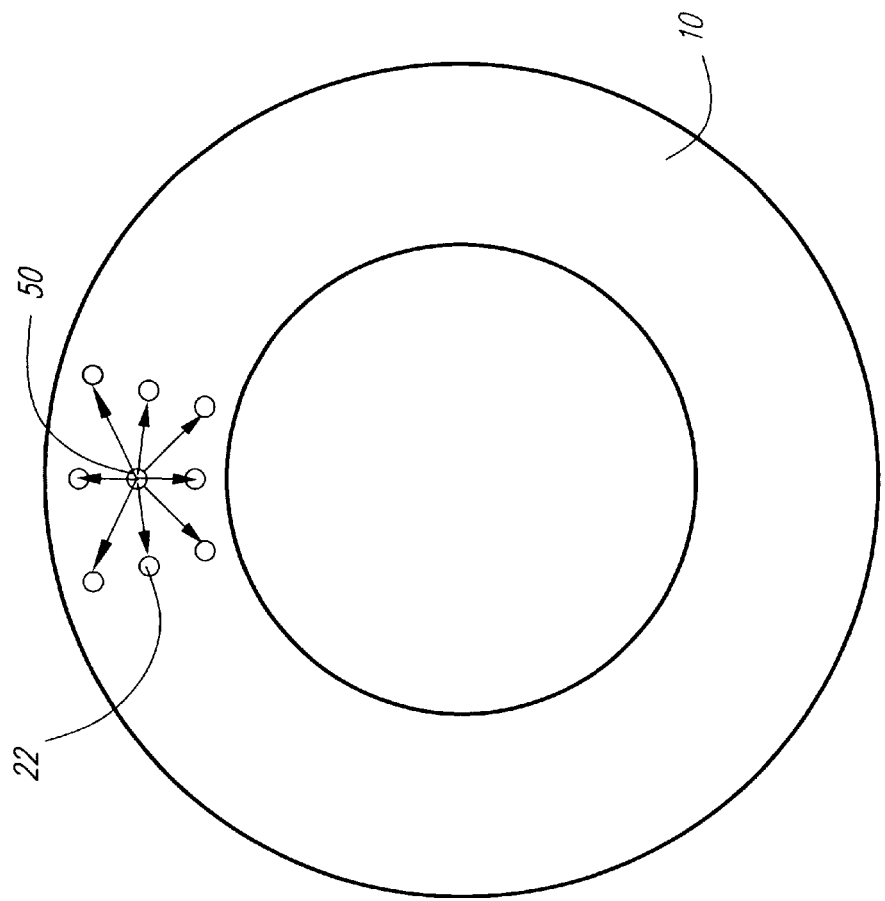
FIG. 4 is a schematic illustration of a scan of the ultrasonic probe for locating cracks extant in the finger dovetails near adjacent pinholes.

Referring to FIG. 4, there is schematically illustrated a demonstration of how the intermediate pinhole of the radial aligned pinholes can be used by the probe to inspect for cracks in the dovetail material adjacent pinholes surrounding the pinhole receiving the probe. Thus, with the probe 40 inserted into an intermediate pinhole 50 as illustrated in FIG. 4 and the ultrasonic beam pulsed circumferentially about the pinhole 50 or physically rotated by mechanical rotation about the probe axis in the pinholes, the dovetail material surrounding the pinholes radially adjacent, as well as those circumferentially adjacent the hole receiving the probe, can be inspected for the formation of cracks. It will also be appreciated that any cracks propagated from the pinhole in which the probe is inserted are difficult to detect. That is, the resolution of the probe is such that cracks in the dovetail material emanating from pinholes adjacent the pinhole receiving the probe are more readily detectable. Consequently, when the ultrasonic inspection is complete and the probe is withdrawn from the pinhole 50, the pinhole 50 itself can be inspected by another method, for example, using eddy currents.

It will also be appreciated that while the material surrounding the radially aligned pinholes on circumferentially opposite sides of the pinhole in which the probe is inserted are inspected as illustrated in FIG. 4, the probe may be used as part of a sampling technique using fewer pinholes (and hence removing fewer pins). That is, by removing pins at greater circumferential distances or intervals about the margin of the wheel, the dovetail materials of the wheel and buckets can be inspected for crack formation as part of a statistical sampling. By sampling for crack formation, the probability of crack formation in a particular wheel and bucket combination can be predicted, with a substantial degree of accuracy. Thus, if the sampling technique reveals no cracks, there is a very high probability that cracks have not developed in the finger dovetails. If only one or more cracks are identified in a sampling technique, there may be only a low probability of additional cracks in the particular wheel/bucket combination undergoing inspection. It is therefore possible to repair only those dovetails in which one or more cracks have been detected with a high degree of assurance that there are no remaining cracks in the wheel/bucket combination. On the other hand, if the sampling reveals a substantial number of cracks, it may be necessary to remove all of the buckets for a more complete inspection of the finger dovetails and repair, as necessary.

It will therefore be appreciated that the present inspection method requires the removal of only a minimum number of pins about the wheel and without the removal of any one or more buckets from the wheel. The inspection method is thus relatively rapid and provides a high sensitivity for the detection of cracks which propagate from pinholes in dovetails of the wheel and buckets.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of inspecting finger dovetails of at least one of a turbine wheel and bucket, the wheel bucket having aligned holes through the finger dovetails for pinning the wheel and bucket to one another, comprising the steps of:

inserting an ultrasonic probe in a hole of said aligned holes in said one of the wheel and the bucket; and rotating the probe within and about axes of the aligned holes to electronically scan material about the hole to identify any cracks extant in the material about the hole.

2. A method according to claim 1 wherein the step of actuating includes scanning the finger dovetail material to identify any cracks extant in the material surrounding a circumferentially or radially adjacent hole.

3. A method according to claim 1 including providing a cylindrically-shaped probe with piezoelectric elements arranged for directing ultrasonic energy in an axial direction, and reflecting the axially directed energy in a generally radial direction.

4. A method of inspecting finger dovetails of at least one of a turbine wheel and bucket, the wheel bucket having aligned holes through the finger dovetails for pinning the wheel and bucket to one another, comprising the steps of:

inserting a phased array ultrasonic probe in a hole of said aligned holes in said one of the wheel and the bucket; and actuating the probe to electronically scan material of a finger dovetail of the one wheel and bucket circumferentially about the hole to identify any cracks extant in the material about the hole.

5. A method according to claim 4 wherein the step of actuating includes steering an ultrasonic beam circumferentially about the hole without mechanically rotating the probe relative to the hole.

6. A method according to claim 4 including providing a cylindrically shaped probe with generally elongated rectilinear piezoelectric elements about the cylindrical surface of the probe.

7. A method according to claim 4 including simultaneously axially inserting the probe into the hole and electronically rotating an ultrasonic beam to produce a continuous helical scan path.

8. A method according to claim 4 including incrementally advancing the probe axially into the hole and electronically rotating the ultrasonic beam to scan the material circumferentially about the hole at each axial hole location to provide circumferential scan paths at axially spaced positions along the length of the hole.

9. A method according to claim 4 wherein the step of actuating includes scanning the finger dovetail material to identify any cracks extant in the material surrounding a circumferentially or radially adjacent hole.

10. A method of inspecting in situ turbine wheel and bucket dovetails for cracks in materials about pinholes containing pins securing the buckets and wheel to one another, comprising the steps of:

(a) removing a pin from a pinhole securing one of said buckets to said wheel;

(b) inserting a phased array ultrasonic probe into the pinhole; and (c) actuating the probe to electronically scan material circumferentially about the pinhole to identify cracks extant in the material about pinholes adjacent to the pinhole receiving the phased array ultrasonic probe.

11. A method according to claim 10 wherein step (c) includes steering an ultrasonic beam circumferentially about the pinhole without mechanically rotating the probe relative to the pinhole.

12. A method according to claim 10 including providing a cylindrically shaped probe with generally elongated rectilinear piezoelectric elements about the cylindrical surfaces of the cylindrical probe.

13. A method according to claim 10 including simultaneously axially inserting the probe into the pinhole and electronically rotating an ultrasonic beam to produce a continuous helical scan path.

14. A method according to claim 10 including incrementally advancing the probe axially into the pinhole and electronically rotating the ultrasonic beam to scan the material circumferentially about the pinhole at each incremental axial location to provide circumferential scan paths at axially spaced positions along the pinhole.

15. A method according to claim 10 wherein each bucket has at least two pinholes and pins for securing the buckets and wheels to one another, and wherein step (a) is limited to at least every other pinhole in a circumferential direction about the wheel and steps (b) and (c) are limited to said at least every other pinhole.

16. A method according to claim 15 including withdrawing the probe from said at least every other pinhole and reinserting a pin into the pinhole.

17. A method according to claim 16 including, prior to reinserting a pin into the pinhole, inspecting the pinhole for cracks.

18. A method according to claim 10 wherein step (c) includes scanning the finger dovetail material to identify any cracks extant in the material surrounding pinholes circumferentially or radially adjacent the pinhole in which the probe is inserted according to step (b).

19. A method according to claim 10 wherein each bucket has three substantially radially aligned pinholes and pins received thereon for securing the buckets and wheels to one another, and wherein step (a) is limited to removing the pin from an intermediate pinhole of the radially aligned pinholes and to at least every other of said intermediate pinholes in a circumferential direction about the wheel and steps (b) and (c) are limited to said at least every other intermediate pinhole.

\* \* \* \* \*